(12) United States Patent
Lin et al.

(10) Patent No.: US 11,751,963 B2
(45) Date of Patent: Sep. 12, 2023

(54) MEDICAL DEVICE FOR MANIPULATING SURGICAL TOOLS

(71) Applicant: Point Robotics Medtech Inc., Hsinchu County (TW)

(72) Inventors: Yun-Chung Lin, Hsinchu County (TW); Xiu-Yun Xiao, Hsinchu County (TW); Ming-Chun Ho, Hsinchu County (TW)

(73) Assignee: POINT ROBOTICS (SINGAPORE) PTE. LTD., Singapore (SG)

( * ) Notice: Subject to any disclaimer, the term of this patent is extended or adjusted under 35 U.S.C. 154(b) by 0 days.

(21) Appl. No.: 17/953,779

(22) Filed: Sep. 27, 2022

(65) Prior Publication Data

US 2023/0018931 A1    Jan. 19, 2023

Related U.S. Application Data

(63) Continuation of application No. 17/138,805, filed on Dec. 30, 2020, now Pat. No. 11,696,809.

(51) Int. Cl.
   *A61B 34/30*   (2016.01)
   *A61B 34/00*   (2016.01)
   *B25J 13/08*   (2006.01)
   *A61B 90/00*   (2016.01)

(52) U.S. Cl.
   CPC .............. *A61B 34/70* (2016.02); *A61B 90/06* (2016.02); *B25J 13/085* (2013.01); *A61B 2090/065* (2016.02)

(58) Field of Classification Search
   CPC . B25J 9/1623; B25J 13/085; A61B 2090/064; A61B 2090/065; A61B 34/70; A61B 90/06
   See application file for complete search history.

(56) References Cited

U.S. PATENT DOCUMENTS

| | | | | |
|---|---|---|---|---|
| 9,561,082 | B2* | 2/2017 | Yen | A61B 34/30 |
| 11,324,557 | B2* | 5/2022 | Shelton, IV | A61B 34/20 |
| 2009/0301253 | A1* | 12/2009 | Nishida | G05B 15/02 |
| | | | | 901/20 |
| 2012/0143084 | A1* | 6/2012 | Shoham | B25J 9/1676 |
| | | | | 901/41 |
| 2013/0096574 | A1* | 4/2013 | Kang | A61B 34/30 |
| | | | | 606/130 |
| 2020/0008889 | A1* | 1/2020 | Ho | A61B 17/34 |

* cited by examiner

*Primary Examiner* — Randell J Krug
(74) *Attorney, Agent, or Firm* — Li & Cai Intellectual Property Office

(57) ABSTRACT

A medical device is provided. The medical device includes an adaptor, a parallel manipulator, a shaft motor, a transmission shaft and a force transducer. The force transducer is disposed between the adaptor and an end platform of the parallel manipulator, and the force transducer has a through hole. The receiving shaft of the adaptor meets the transmission shaft in the through hole to receive the mechanical force from the transmission shaft to manipulate movement of the surgical tool.

12 Claims, 11 Drawing Sheets

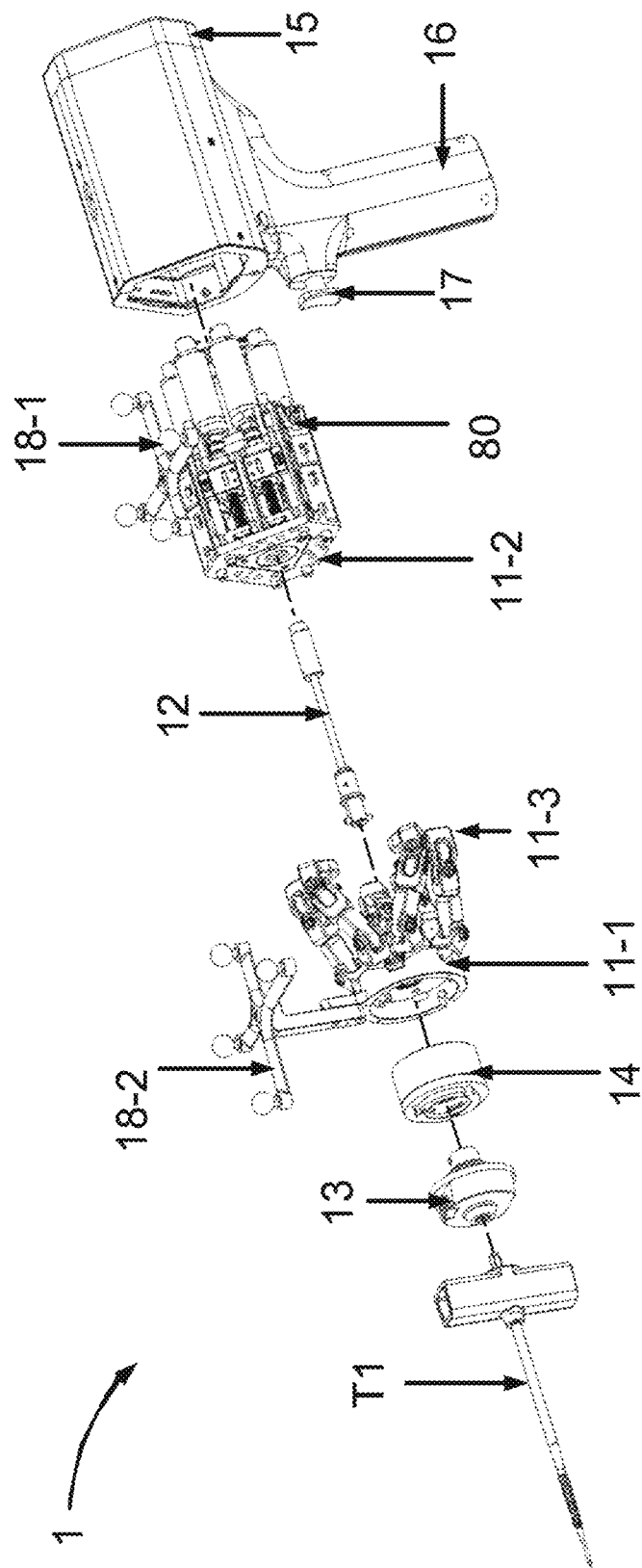

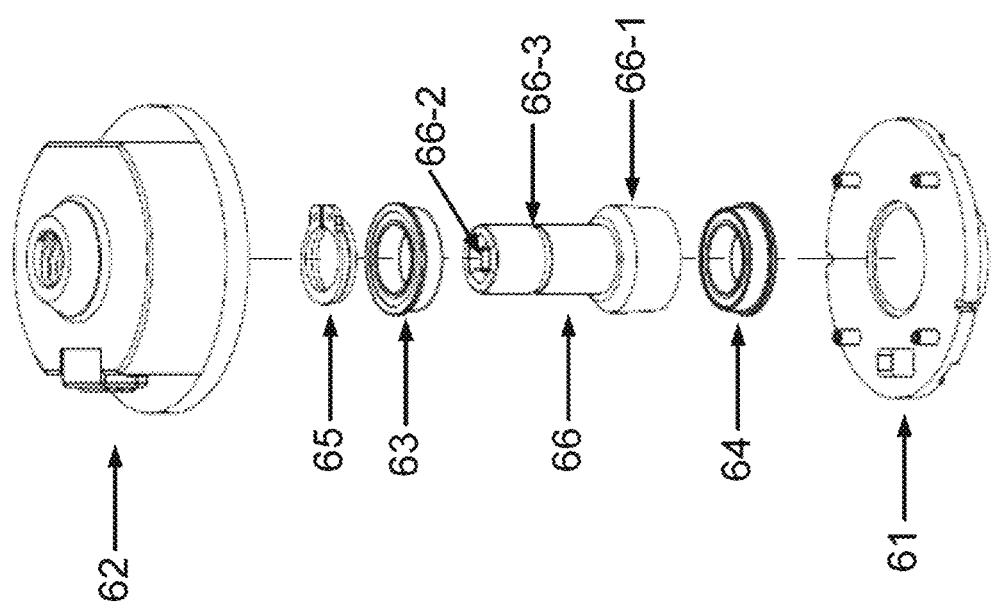

MEDICAL DEVICE FOR MANIPULATING SURGICAL TOOLS

CROSS-REFERENCE TO RELATED PATENT APPLICATION

This application is a continuation application of the U.S. application Ser. No. 17/138,805, filed on Dec. 30, 2020 and entitled "MEDICAL DEVICE FOR MANIPULATING SURGICAL TOOLS", now pending, the entire disclosures of which are incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure generally relates to medical device, and more particularly to a medical device having a transmission shaft between an end platform and base platform of a parallel manipulator and configured to transfer mechanical force.

BACKGROUND OF THE DISCLOSURE

A parallel mechanism is capable of positioning and orienting an end platform with up to six or more degrees of freedom. The end platform of a parallel mechanism can be used to support a medical device, such as a diagnostic device or a surgical instrument. Since the end platform parallel mechanism can be made extremely small, the mechanism can be used either for surgery through a large surgical opening or for endosurgery through a small surgical opening or body orifice.

Because the end platform is capable of being manipulated with high accuracy and dexterity, the parallel mechanism is particularly suitable for use in surgery by remote control. The ability of the mechanism to adjust the position of the end platform makes the mechanism suitable for medical applications that require precision and fine motions. However, having a motor for controlling the surgical tool mounted at the end platform can cause additional weight and force to be applied to the end platform during operation. The additional weight and force may affect the response time and the precision of the range/path of the planned operation. Therefore, in order to increase the precision of the medical device, there is a need to minimize the force influencing the end platform of the parallel manipulator.

SUMMARY OF THE DISCLOSURE

In response to the above-referenced technical inadequacies, the present disclosure provides a medical device with a transmission shaft.

In one aspect, the present disclosure provides a medical device that includes: a parallel manipulator having an end platform and a base platform mechanically coupled to the end platform; an adaptor having a body detachably coupled to the end platform and a receiving shaft rotatably supported by the body, the receiving shaft having a receiving yoke; a transmission shaft rotatably supported by the end platform, the transmission shaft having a transmission yoke configured to transfer mechanical force to the receiving yoke, a pliable rod coupled to the transmission yoke, and a runner coupled to the pliable rod; and a shaft motor configured to generate mechanical force to drive the transmission shaft, the shaft motor having a drive shaft slidably engaged to the runner.

In another aspect, the present disclosure provides a medical device that includes: a parallel manipulator having an end platform and a base platform mechanically coupled to the end platform; a sensor system mechanically attached to the end platform; an adaptor detachably coupled to the sensor system, the adaptor having a body and a receiving shaft rotatably supported by the body; a transmission shaft rotatably supported by the end platform and configured to transfer mechanical force to the receiving shaft; and a shaft motor drivingly connected to the transmission shaft and configured to transfer mechanical force to the transmission shaft.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which:

FIG. 3 illustrates an exploded view of a medical device according to some embodiments of the instant disclosure;

FIG. 6 illustrates an exploded view of an adaptor according to some embodiments of the instant disclosure;

DETAILED DESCRIPTION OF THE EXEMPLARY EMBODIMENTS

Figure 1:
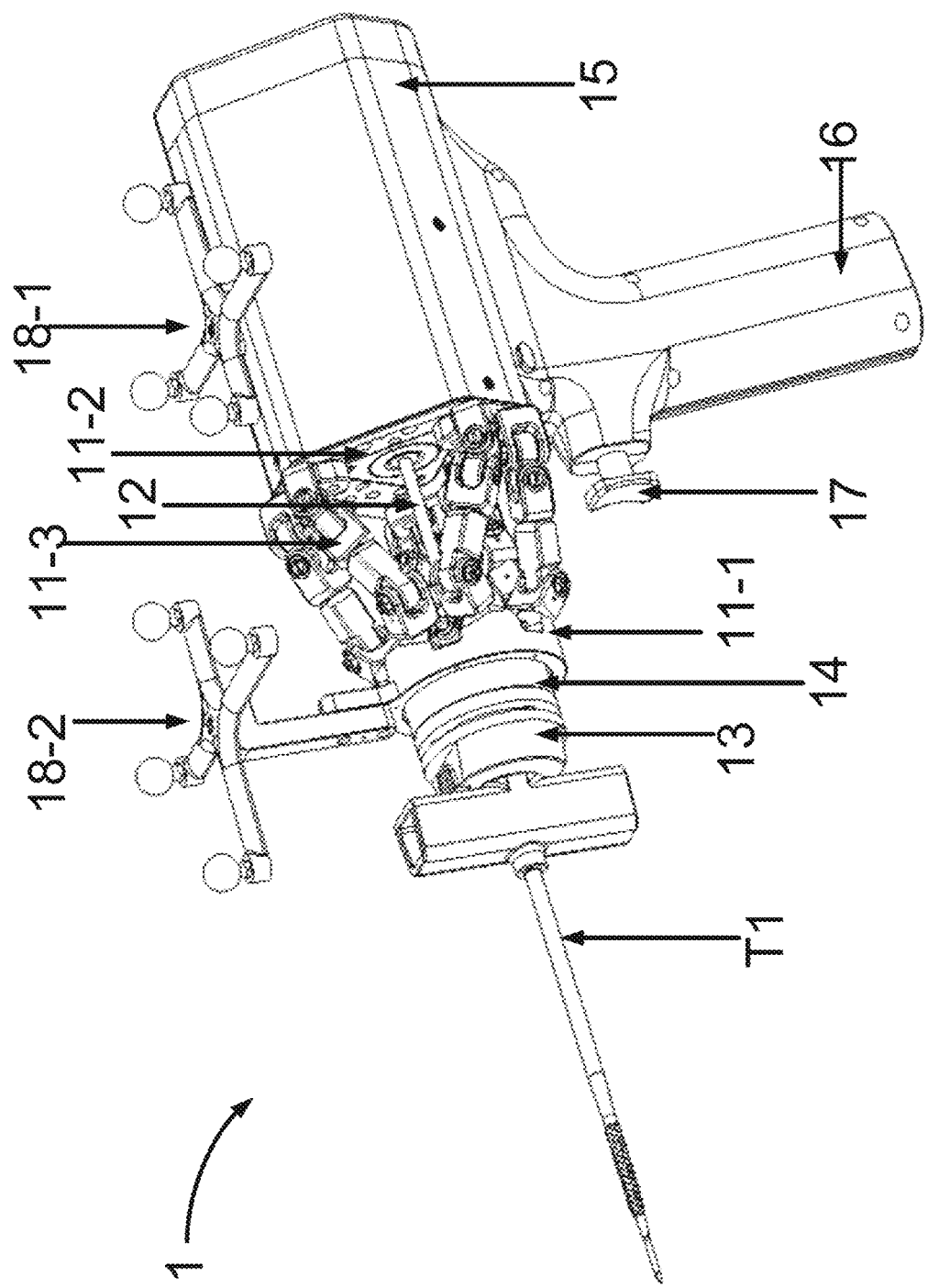
FIG. 1 illustrates a 3D representation view of a medical device according to some embodiments of the instant disclosure.

The present disclosure will now be described more fully hereinafter with reference to the accompanying drawings, in which exemplary embodiments of the disclosure are shown. This disclosure may, however, be embodied in many different forms and should not be construed as limited to the exemplary embodiments set forth herein. Rather, these exemplary embodiments are provided so that this disclosure will be thorough and complete, and will fully convey the scope of the disclosure to those skilled in the art. Like reference numerals refer to like elements throughout.

The terminology used herein is for the purpose of describing particular exemplary embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 2:
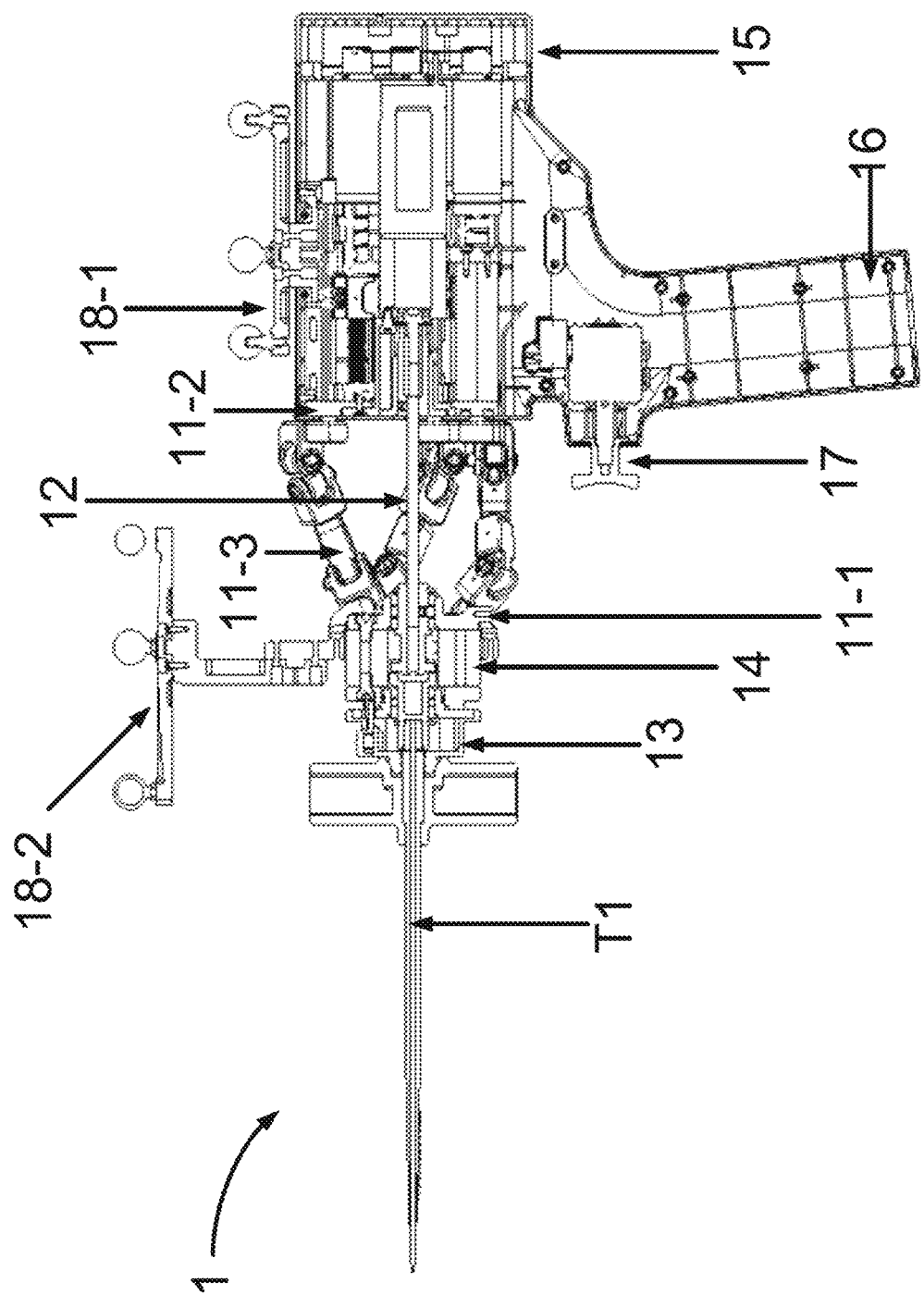
FIG. 2 illustrates a cross-sectional view of a medical device according to some embodiments of the instant disclosure.

FIG. 1 illustrates a 3D representation view of a medical device according to some embodiments of the instant disclosure. FIG. 2 illustrates a cross-sectional view of a medical device according to some embodiments of the instant disclosure. FIG. 3 illustrates an exploded view of a medical device according to some embodiments of the instant disclosure. In some embodiments, the medical device 1 includes a parallel manipulator, a transmission shaft 12, and an adaptor 13. The parallel manipulator includes an end platform 11-1, a base platform 11-2, and a plurality of limbs 11-3 operably coupled between the end platform 11-1 and the base platform 11-2. The transmission shaft 12 is disposed between the end platform 11-1 and the base platform 11-2. Further, the transmission shaft 12 is rotatably supported by the end platform 11-1. In some embodiments, the adaptor 13 is configured to hold a surgical tool T1, such as a drill bit, a trocar, or a saw blade. In some embodiments, the medical device 1 further includes a sensor system 14 disposed between the adaptor 13 and the end platform 11-1. The sensor system 14 is configured to monitor the force exerted and received by the adaptor 13.

In some embodiments, the medical device 1 further includes a housing 15, a handle 16, and a control module 17. The base platform 11-2 is mechanically attached to the housing 15 and accommodates a machine module 19 configured to manipulate the movement of the plurality of limbs 11-3, which in turn control the movement of the end platform 11-1. The machine module 19 includes a plurality of actuators for correspondingly manipulating the plurality of limbs 11-3 and a shaft motor for manipulating the transmission shaft 11-2. The handle 16 allows user to hold onto and maneuver the medical device 1 during operation. The control module 17 allows the user to trigger, halt, or adjust actions of the surgical tool T1 or perform other functions of the medical device 1.

Parallel manipulators may be classified based on degree of freedom, number of limbs, order of joints in each limb, and type of actuator. In some embodiments, the parallel manipulator can be a hexa parallel manipulator with six degrees of freedom (6-DOF). In some embodiments, the plurality of limbs 11-3 comprises six limbs. In some embodiments, each limb 11-3 has a first joint coupled to an actuator underneath the base platform 11-2, a second joint coupled to the end platform 11-1, and a third joint between the first joint and the second joint. In some embodiments, the parallel manipulator is a 6-PUS parallel manipulator. In some embodiments, the first joint is a prismatic joint. In some embodiments, the second joint is a spherical joint. In some embodiments, the third joint is a universal joint. The universal joint is formed using two revolute joint.

In some embodiments, the medical device 1 further includes a first positioning unit 18-1 and a second positioning unit 18-2. The first positioning unit 18-1 and the second positioning unit 18-2 correspondingly includes a plurality of markers for emitting electromagnetic signals, sound wave, heat, or other perceivable signals, and adaptors for mounting the markers at particular orientations with respect to the body of the device. In some embodiments, the markers and adaptors are used in cooperation with a spatial sensor for object tracking functionalities during operation. The second positioning unit 18-2 may be disposed in an area between the adaptor 13 and the end platform 11-1. In some embodiments, the second positioning unit 18-2 is disposed on the end platform 11-1. In some other embodiments, the second positioning unit 18-2 is disposed on the adaptor 13. In some other embodiments, the second positioning unit 18-2 is disposed on the tool T1.

Figure 4A:
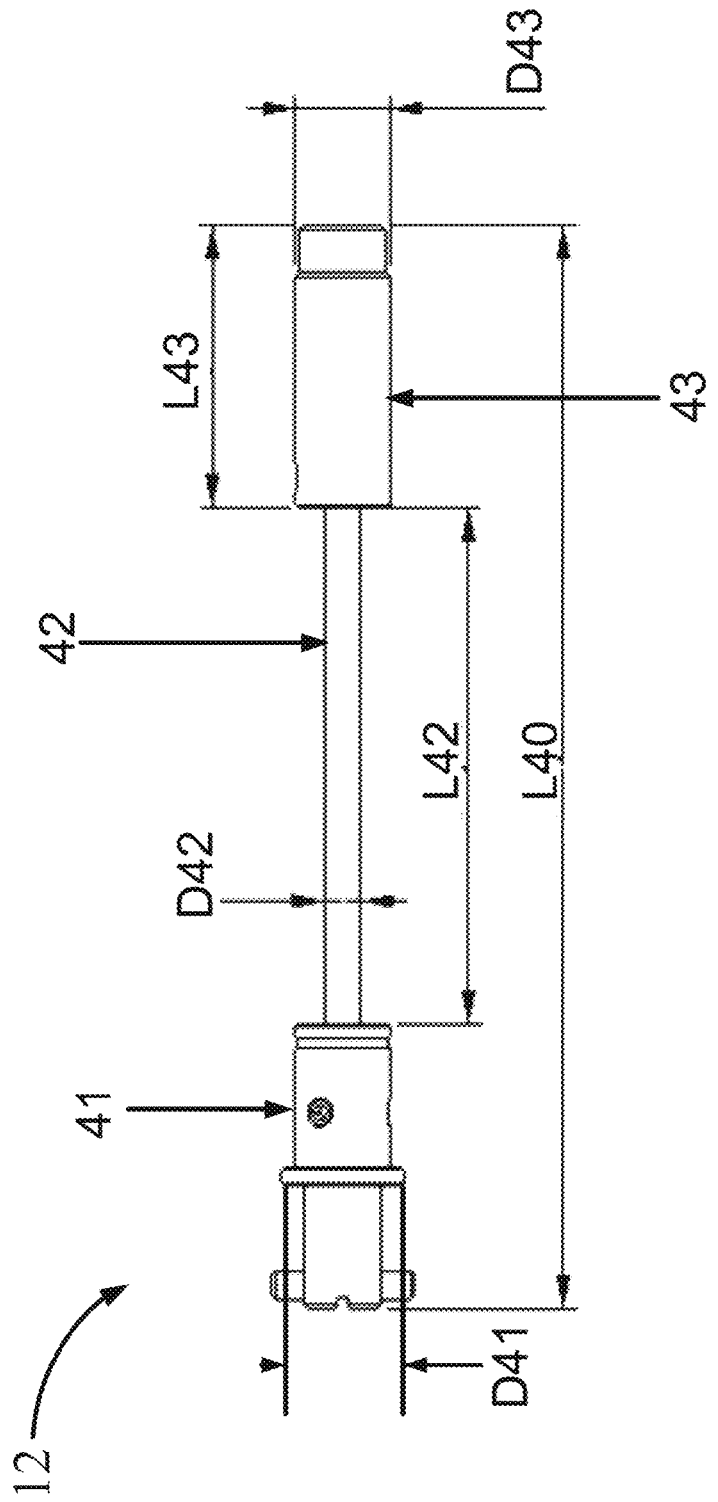
FIG. 4A illustrates a perspective view of a transmission shaft according to some embodiments of the instant disclosure.
Figure 4B:
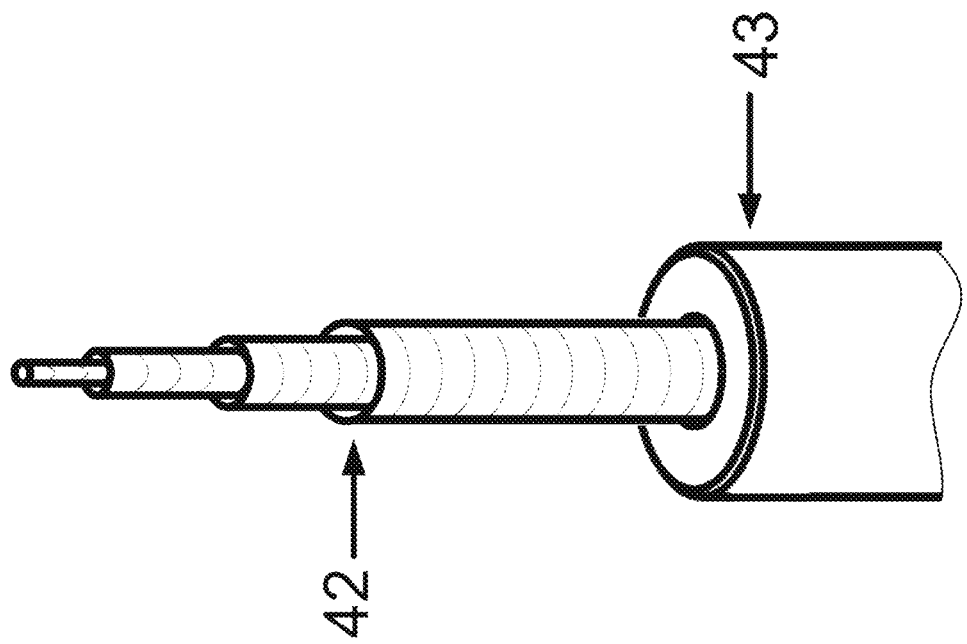
FIG. 4B illustrates a sectional view of a transmission shaft according to some embodiments of the instant disclosure.

FIG. 4A illustrates a perspective view of a transmission shaft according to some embodiments of the instant disclosure. FIG. 4B illustrates a sectional view of a transmission shaft according to some embodiments of the instant disclosure. In some embodiments, the transmission shaft 12 is rotatably supported by the end platform and slidingly engaged to the base platform. In some embodiments, the transmission shaft 12 includes a transmission yoke 41 configured to transfer a mechanical force to a surgical tool (i.e. surgical tool T1 in FIG. 1), a pliable rod 42 coupled to the transmission yoke 41, and a runner 43 coupled to the pliable rod 42. In some embodiments, the pliable rod 42 is an elastic structure. The pliable rod 42 structurally adapts to the applied force and returns to original structure when force is removed. The pliable rod 42 is stiff enough to endure and transfer the mechanical force from the shaft motor. In an exemplary embodiment, the pliable rod 42 is a spring tube having a plurality of layers. In some embodiments, the pliable rod 42 has four layers (i.e. pliable rod 42 in FIG. 4B). In some embodiments, a maximum distance between the end platform and the base platform is greater than a length of the pliable rod, and a minimum distance between the end platform and the base platform is substantially same as a length of the pliable rod. In this way, the pliable rod does may not experience stress when the medical device is not in use.

In some embodiments, during operation of the medical device, only the pliable rod is exposed between the end platform and the base platform when the end platform and the base platform are at minimum distance from each other. In some other embodiments, during operation of the medical device, the pliable rod and a portion of the runner is exposed between the end platform and the base platform when the end platform and the base platform are at minimum distance from each other. In other words, the runner is substantially planar to the base platform when the end platform and the base platform are at minimum distance from each other.

On the other hand, a portion of the runner is exposed between the end platform and the base platform when the distance between the end platform and the base platform are greater than minimum distance. When the end platform and the base platform are at maximum distance from each other, an overlap between the runner and the drive shaft is no less than 5 mm. However, in some other embodiments, an overlap between the runner and the drive shaft may be less than 5 mm at maximum distance between the end platform and the base platform. In other words, a minimum overlap between the runner and the drive shaft is no more than 5 mm. During operation, a force may be applied to the pliable rod causing distortion. The elasticity of the pliable rod allows an angle deviation of 30° from a central axis of a runner without being deformed upon removal of the applied force.

In some embodiments, the runner is substantially planar to the base platform when the end platform and the base platform are at minimum distance from each other. Further, the length of the pliable rod is substantially same as minimum distance between the end platform and the base platform. In some other embodiments, the runner is protruding the base platform when the end platform and the base platform are at minimum distance from each other. Further, the length of the pliable rod is less than minimum distance between the end platform and the base platform. In some other embodiments, the runner is recessed from the base platform when the end platform and the base platform are at minimum distance from each other. Further, the length of the pliable rod is greater than minimum distance between the end platform and the base platform. However, during minimum distance between the end platform and the base platform, the pliable rod is at normal state. In some embodiments, the normal state of the pliable rod is a state in which the pliable rod experiences relatively no force. Thus, the pliable rod maintains its original shape (i.e. not stretched, bent, or compressed) during normal state.

In an exemplary embodiment, a length L40 of the transmission shaft 12 is substantially 11.5 cm (i.e. 11.495 cm). In an exemplary embodiment, a length L42 of the pliable rod 42 is substantially 5.5 cm (i.e. 5.475 cm). In an exemplary embodiment, a diameter D42 of the pliable rod 42 is substantially 0.38 cm. In an exemplary embodiment, a diameter D43 of the runner 43 is substantially 1 cm. In an exemplary embodiment, a length L43 of the runner 43 is substantially 3 cm (i.e. 2.995 cm). In an exemplary embodiment, a diameter D41 of a widened part of the transmission yoke 41 is substantially 1.3 cm. However, the above-mentioned measurements are only examples, and should not be used to limit the scope of the disclosure.

Figure 5:
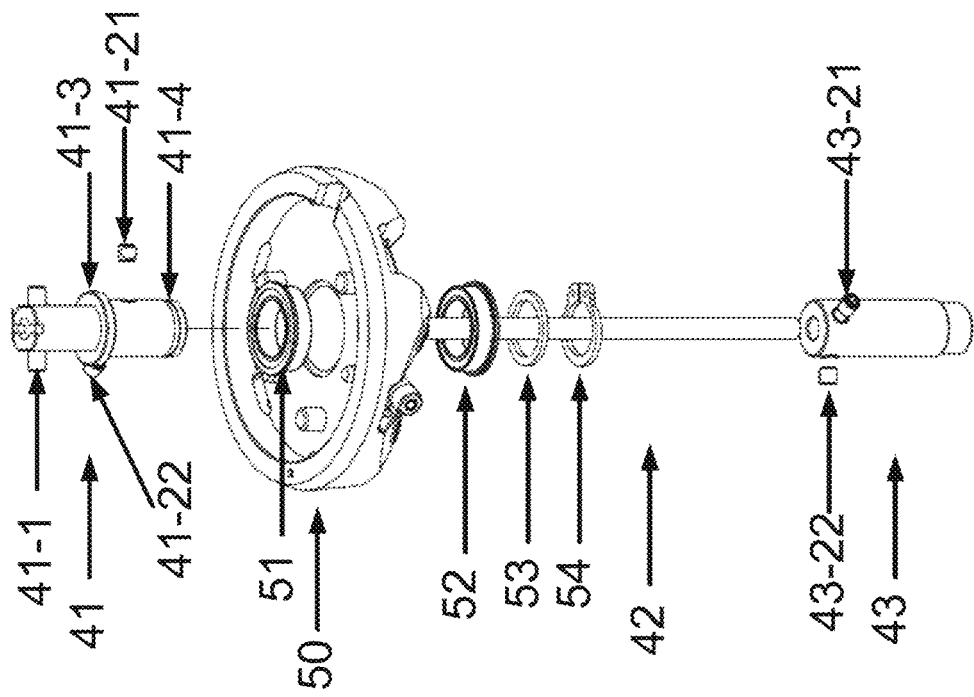
FIG. 5 illustrates an exploded view of a transmission shaft according to some embodiments of the instant disclosure.

FIG. 5 illustrates an exploded view of a transmission shaft according to some embodiments of the instant disclosure. In some embodiments, the transmission yoke 41 and the runner 43 correspondingly have a through hole in which the pliable rod 42 is inserted. To physically attach the pliable rod 42 to the transmission yoke 41 and the runner 43, pins 41-21, 41-22, 43-21, and 43-22 are correspondingly used. The pins 41-21 and 41-22 are used to pin or press one end of the pliable rod 42 to an inner surface of the through hole of the transmission yoke 41. In some embodiments, the pins 41-21 and 41-22 are disposed orthogonally from each other. Thus, the pliable rod 42 may be disposed partial to one side of the transmission yoke 41. The pins 43-21 and 43-22 are used to pin or press another end of the pliable rod 42 to an inner surface of the through hole of the runner 43. In some embodiments, the pins 43-21 and 43-22 are disposed orthogonally from each other. Thus, the pliable rod 42 may be disposed partial to one side of the runner 43. Although the pliable rod 42 may be off centered corresponding to the transmission yoke 41 and the runner 43, the orthogonal positioning of the pins 41-21, 41-22, 43-21, and 43-22 ensure that the pliable rod 42 is securely fastened to the transmission yoke 41 and the runner 43 during operation.

In some embodiments, the transmission yoke 41 includes a protrusion 41-1 configured to transfer a mechanical force to a receiving shaft of the adaptor (i.e. adaptor 13 in FIG. 1). The protrusion 41-1 is configured to have minimal contact to the receiving shaft of the adaptor during operation to prevent noise (meaningless or unwanted mechanical force input) on the adaptor.

As shown in FIG. 5, the end platform 50 includes a first bearing 51 and a second bearing 52. In some embodiments, the end platform 50 further includes a washer 53 and a retaining ring 54. In some embodiments, the first bearing 51 and the second bearing 52 are flanged bearing wherein an extension or a lip on the outer ring of the bearing is designed to aid the mounting and positioning of the bearing. In some embodiments, a flange of the first bearing 51 is positioned on a surface of the end platform 50 facing away from the base platform (i.e. positioning between the end platform 11-1 and the adaptor 13 in FIG. 3). In some embodiments, a flange of the second bearing 52 is positioned on a surface of the end platform 50 facing towards the base platform (i.e. positioning between the end platform 11-1 and the base platform 11-2 in FIG. 3).

In some embodiments, the retaining ring 54 is radially installed on a groove 41-4 of the transmission yoke 41. The retaining ring 54 may be a C-ring. In some embodiments, the washer 53 is disposed between retaining ring 54 and the second bearing 52 to prevent abrasion of the second bearing 52. Further, the washer 53 is used to fill the gap between the flange 41-3 of the transmission yoke 41 and retaining ring 54. In some embodiments, the gap between the flange 41-3, the end platform 50, the washer 53, the first bearing 51, and the second bearing 52 is substantially removed through the use of the retaining ring 54. The bearings 51 and 52 may be sandwiched between the flange 41-3 of the transmission yoke 41 and the retaining ring 54. Thus, the flange 41-3 of the transmission yoke 41 and the retaining ring 54 are used to aid the mounting and positioning of the transmission yoke 41.

FIG. 6 illustrates an exploded view of an adaptor according to some embodiments of the instant disclosure. In some embodiments, the adaptor includes a body and a receiving shaft 66 disposed within and rotatably supported by the body. The body includes a base 61 and a cover 62 mechanically attached to the base 61. The receiving shaft 66 is disposed between the base 61 and the cover 62. In some embodiments, the receiving shaft 66 includes a receiving yoke 66-1 and a chuck 66-2 opposite the receiving yoke 66-1. The chuck 66-2 is configured to hold a surgical tool (i.e. surgical tool T1 in FIG. 1). The chuck 66-2 is aligned with a through hole of the cover 62 where a surgical tool may be inserted. The receiving yoke 66-1 is exposed outside of the adaptor. In this way, receiving yoke 66-1 can receive mechanical force from the transmission shaft. The contact between the receiving yoke 66-1 and the transmission shaft is designed to be as minimal as possible to prevent generation of noise. In some embodiments, a groove (not shown)

is formed on the receiving yoke 66-1 complementary to a protrusion (i.e. protrusion 41-1 in FIG. 5) of the transmission shaft for receiving the mechanical force.

In some embodiments, the adaptor further includes a first bearing 63 and a second bearing 64. In some embodiments, the first bearing 63 and the second bearing 64 are flanged bearing in which an extension or a lip on the outer ring of the bearing is designed to aid the mounting and positioning of the bearing. In some embodiments, a flange of the first bearing 63 is positioned on a surface of the base 61 facing towards the cover 62. In some embodiments, a flange of the second bearing 64 is positioned on a surface of the base 61 facing away from the cover 62.

In some embodiments, the adaptor further includes a retaining ring 65. In some embodiments, the retaining ring 65 is radially installed on a groove 66-3 of the receiving shaft 66. The retaining ring 65 may be a C-ring. In some embodiments, a diameter of the receiving yoke 66-1 is greater than a diameter of the chuck 66-2. In this way, the receiving yoke 66-1 has a wider diameter than an inner ring of the bearings 63 and 64. The bearings 63 and 64 may be sandwiched between the receiving yoke 66-1 and the retaining ring 65. Thus, the receiving yoke 66-1 and the retaining ring 65 are used to aid the mounting and positioning of the receiving shaft 66.

Figure 7:
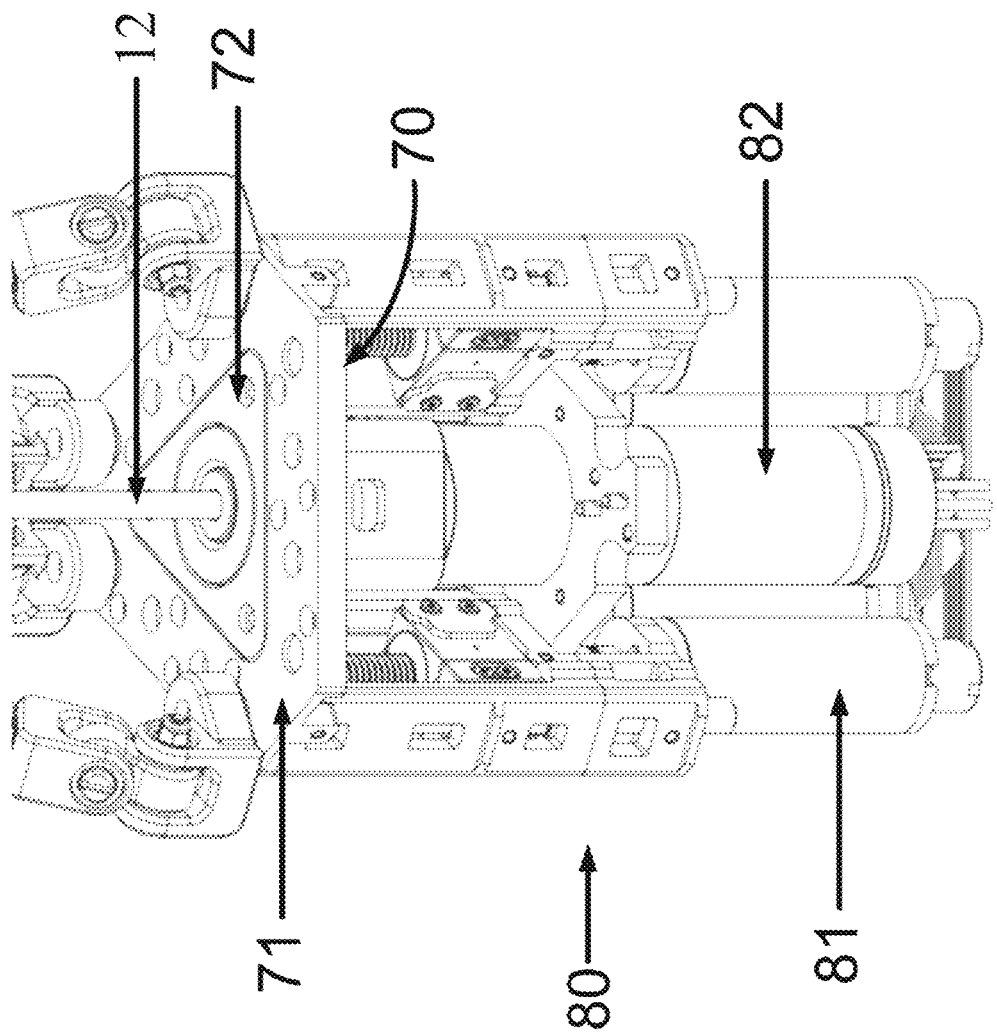
FIG. 7 illustrates a perspective view of a machine module according to some embodiments of the instant disclosure.

FIG. 7 illustrates an isometric view of a machine module according to some embodiments of the instant disclosure. In some embodiments, the machine module 80 is mechanically attached to a base platform 70 of a parallel manipulator. In some embodiments, machine module 80 includes a plurality of actuators 81 configured to control the movement of the plurality of limbs (i.e. limbs 11-3 in FIG. 1) of the parallel manipulator and a shaft motor 82 configured to generate a mechanical force for manipulating a surgical tool (i.e. surgical tool T1 in FIG. 1).

In some embodiments, as shown in FIG. 7, the base platform 70 includes a limb base 71 and a shaft base 72 surrounded by the limb base 71. The limb base 71 is used to provide structural support between the plurality of limbs of the parallel manipulator and the actuators 81 of the machine module 80. The shaft base 72 is used to provide structural support for the shaft motor 82. In some embodiments, a transmission shaft 12 is disposed within a recess area of the shaft base 72. A portion of the shaft motor 82 may be exposed in the recess area of the shaft base 72. The transmission shaft 12 and the shaft motor 82 may be slidingly engaged within the recess area of the shaft base 72.

Figure 8:
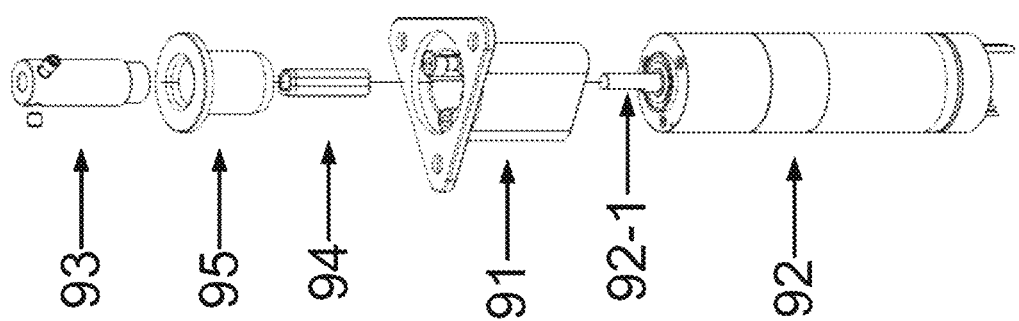
FIG. 8 illustrates an exploded view of a transmission shaft, a parallel manipulator, and a machine module according to some embodiments of the instant disclosure.

FIG. 8 illustrates an exploded view of a transmission shaft, a parallel manipulator, and a machine module according to some embodiments of the instant disclosure. A shaft motor 92 of the machine module is coupled the shaft base 91 of the parallel manipulator. In some embodiments, a rotor 92-1 of the shaft motor 92 is inserted into a recess area of the shaft base 91. A drive shaft 94 is attached to rotor 92-1 and configured to move in a same direction as the rotor 92-1. A runner 93 of a transmission shaft is slidingly engaged to the shaft motor 92. In some embodiments, the runner 93 is slidingly engaged to the drive shaft 94, in which the mechanical force generated by the shaft motor is transferred to the runner 93 through the drive shaft 94. The runner 93 has a socket and a sectional shape profile of the drive shaft 94 is structurally complementary to a sectional shape profile of the socket. The socket is configured to slide along the drive shaft 94. Further illustration and related explanation for the relation between the drive shaft and the runner shall be disclosed in FIG. 9.

In some embodiment, a barrel 95 is placed within a recess area of the shaft base 91. The barrel 95 is surrounding the runner 93, while the runner 93 is surrounding the drive shaft 94 when the medical device is assembled. The barrel 95, the runner 93, and the drive shaft 94 are successively fitted within each other.

In some embodiments, to reduce friction between the runner 93 and the drive shaft 94, a material of the runner 93 and the drive shaft 94 are different from each other. A young's modulus of the drive shaft 94 is different from a young's modulus of the runner 93. In some embodiments, a material of the runner 93 is steel and a material of the drive shaft 94 is copper. In some embodiments, a material of the runner 93 and the drive shaft 94 are ant-friction metal-polymers.

In some embodiments, to reduce friction between the runner 93 and the drive shaft 94, a lubricant is coated on an outer surface of the drive shaft 94. In some embodiments, a lubricant is coated on an inner surface of the runner 93. The lubricant may include, at least one of, carbon powder, lubricating oil, etc.

In some embodiments, to reduce friction between the runner 93 and the barrel 95, a material of the runner 93 and the barrel 95 are different from each other. A young's modulus of the runner 93 is different from a young's modulus of the barrel 95. In some embodiments, a material of the runner 93 is steel and a material of the barrel 95 is copper. In some embodiments a material of the runner 93 and the barrel 95 are ant-n friction metal-polymers.

In some embodiments, to reduce friction between the runner 93 and the barrel 95, a lubricant is coated on an outer surface of the runner 93. In some embodiments, a lubricant is coated on an inner surface of the barrel 95. The lubricant may include, at least one of, carbon powder, lubricating oil, etc.

Figure 9:
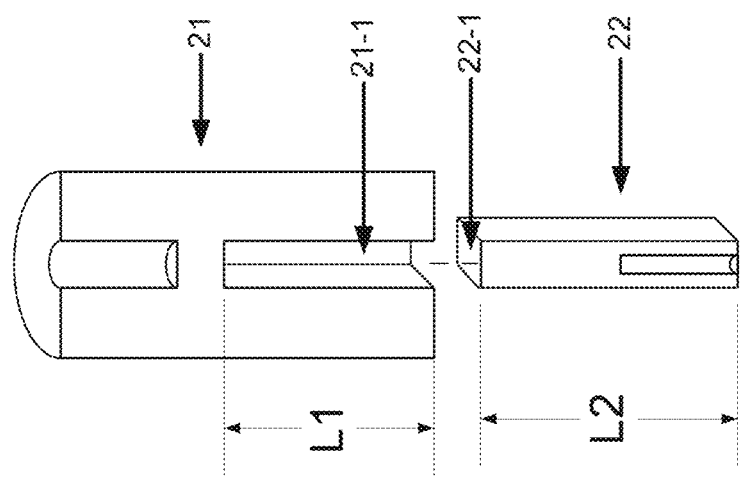
FIG. 9 illustrates a cross-sectional view of a drive shaft and a runner according to some embodiments of the instant disclosure.

FIG. 9 illustrates a cross-sectional view of a drive shaft and a runner according to some embodiments of the instant disclosure. A representative illustration of the runner 21 and the drive shaft 22 is provided to assist in description sliding engagement therebetween. The runner 21 has a socket 21-1. A sectional shape profile of a surface 22-1 of the drive shaft is structurally complementary to a sectional shape profile of the socket 21-1. The socket 21-1 is configured to slide along the drive shaft 22 when required during operation of the medical device. In some other embodiments, an overlap between the drive shaft 22 and the runner 21 is needed during operation to ensure the transfer of mechanical force therebetween. The overlap between the drive shaft 22 and the runner 21 is no less than 5 mm during operation to ensure the transfer of mechanical force therebetween. In some other embodiments, a minimum overlap between the drive shaft 22 and the runner 21 is no more than 5 mm. In some other embodiments, a minimum overlap between the drive shaft 22 and the runner 21 ranges between 0 to 5 mm. In some further embodiments, a minimum overlap between the drive shaft 22 and the runner 21 ranges between 5 mm to 100 mm. In some embodiments, the depth L1 of the socket 21-1 is greater than the height L2 of the drive shaft 22. In some other embodiments, the depth L1 of the socket 21-1 is substantially the same as the height L2 of the drive shaft 22.

In some embodiments, the sectional shape profiles of the socket 21-1 and the surface 22-1 of the drive shaft 22 are a polygonal shape profile. The drive shaft 22 have a plurality of facets that meet each other to form angled intersection. In some embodiments, an intersection between two facets are rounded or curved to prevent damage during insertion. The socket 21-1 is an enclosed opening that grips the faces of the drive shaft 22. The angle between facets of the drive shaft 22 provide grip to drive the runner 21.

In some other embodiments, the drive shaft and the runner have different structure used in transferring mechanical force. The drive shaft has a protrusion. The runner has a groove corresponding to the protrusion. In an assembled medical device, the protrusion of the drive shaft is inserted into the groove of the runner. The height of groove is enough to allow the protrusion to stay within the groove while the runner slides away from the drive shaft during operation. The protrusion is configured to slide along the corresponding groove. Further, the drive shaft is configured to transfer a mechanical force to the runner through a sidewall of the protrusion of drive shaft tangential to an inner sidewall of the groove of the runner when in motion.

In some embodiments, drive shaft has two protrusions extending in opposite direction from each other. The runner has two grooves complementary to the two protrusions of the drive shaft. In some embodiments, drive shaft has a dogbone drive joint and the runner is a drive cup.

Figure 10:
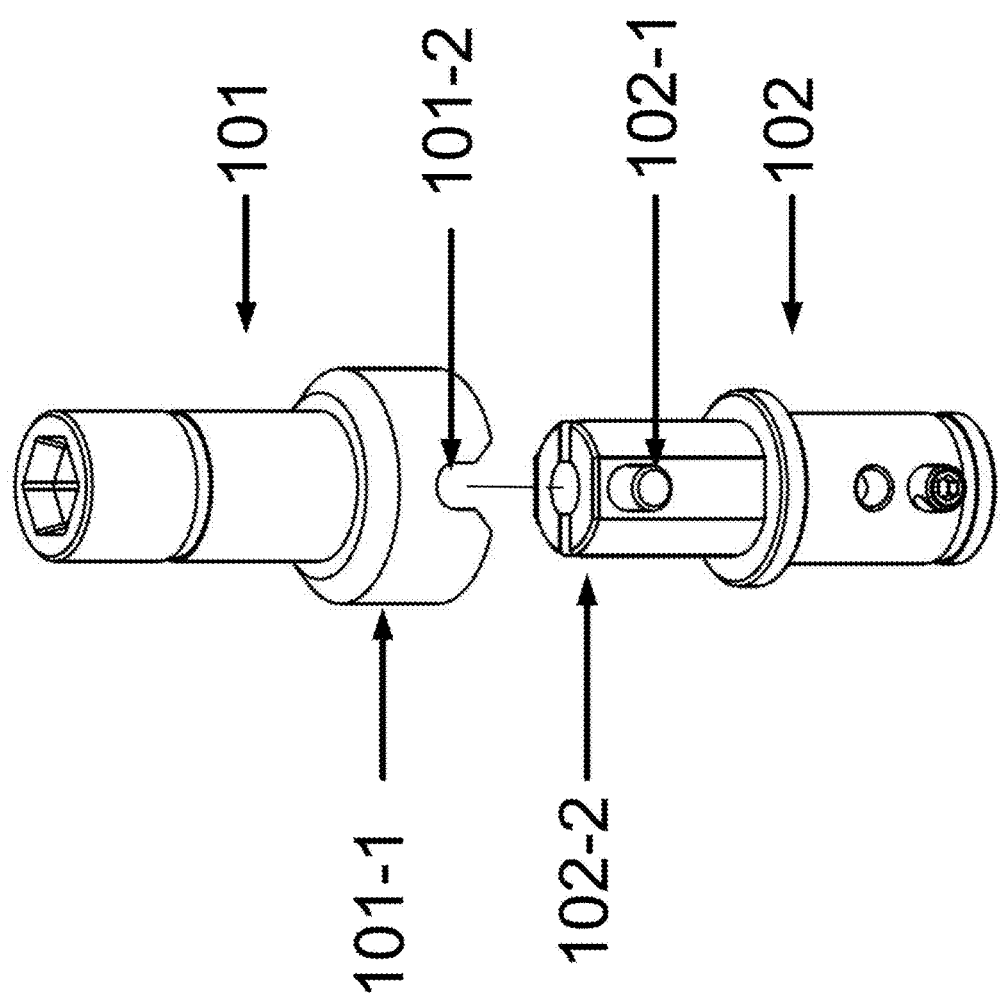
FIG. 10 illustrates a perspective view of a receiving shaft and a transmission yoke according to some embodiments of the instant disclosure.

FIG. 10 illustrates a perspective view of a receiving shaft and a transmission yoke according to some embodiments of the instant disclosure. In some embodiments, a transmission yoke 102 of the transmission shaft has at least one protrusion 102-1. The at least one protrusion 102-1 is extending from a body 102-2 of the transmission yoke 102. In some embodiments, the protrusion 102-1 is cylindrical in shape. The receiving shaft 101 has a receiving yoke 101-1. The receiving yoke 101-1 has grooves 101-2 structurally complementary to the at least one protrusion 102-1 of the transmission yoke 102. Upon assembly of the medical device, a top portion of the body 102-2 is inserted in a recessed area of the receiving yoke 101-1. During operation, the transmission yoke 102 is configured to transfer a mechanical force to the receiving yoke 101-1 through a sidewall of the protrusion 102-1 tangential to an inner sidewall of the groove 101-2. In this way, the contact between the receiving yoke 101-1 and the transmission yoke 102 is minimal during operation to prevent the transmission yoke 102 from generating unwanted noise.

In some embodiments, the transmission yoke 102 has two protrusions 102-1. The protrusions 102-1 are extending from sidewall of the transmission yoke 102 in opposite direction from each other. The two protrusions 102-1 are 180° apart from each other. The receiving yoke 101-1 has two grooves 101-2 complementary to the two protrusions 102-1. In the same way as the two protrusions 102-1, the two grooves 101-2 are disposed opposite of each other. In some embodiments, transmission yoke 102 is a dogbone drive joint and the receiving yoke 101-1 is a drive cup.

Figure 11:
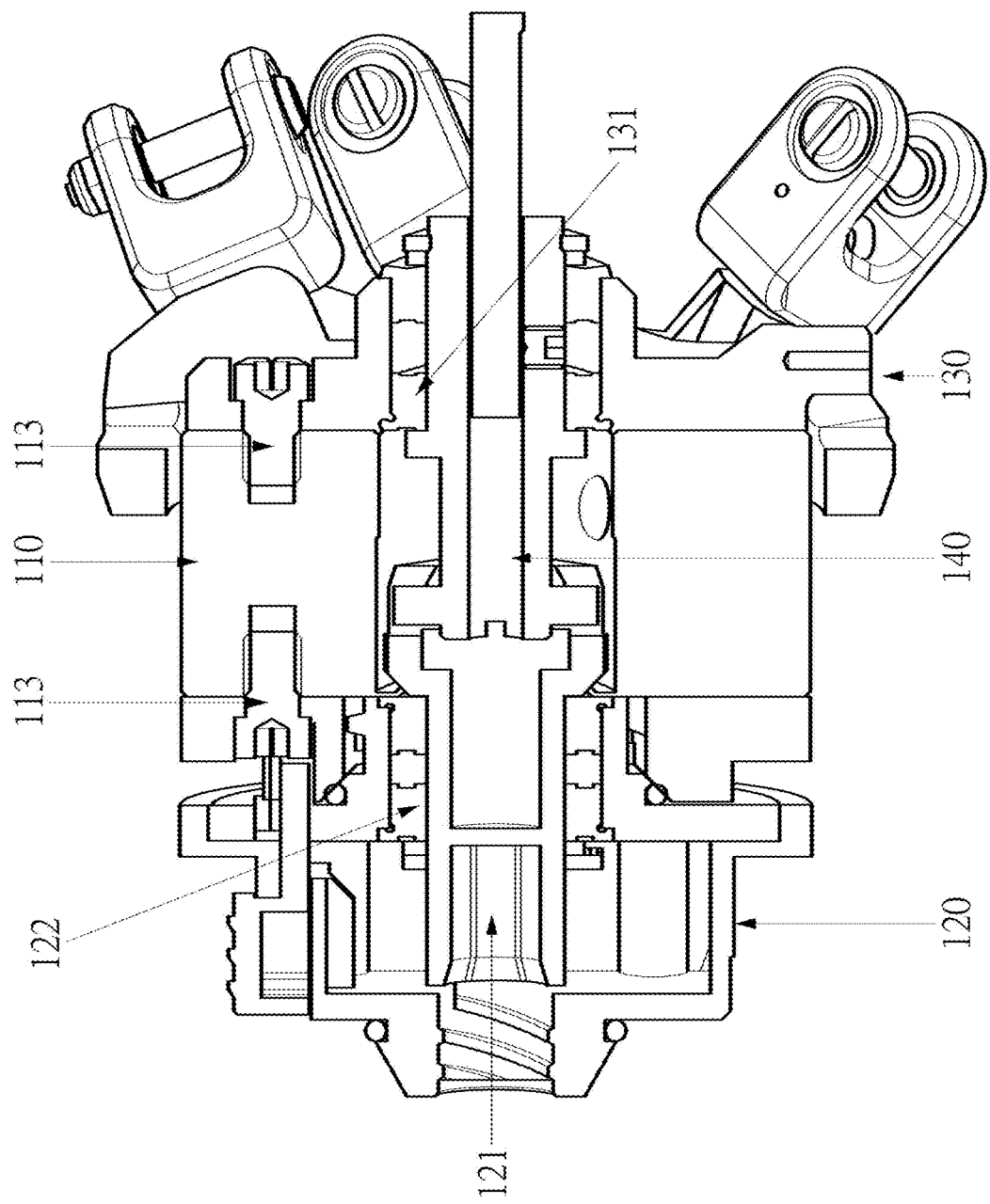
FIG. 11 illustrates a cross-sectional view of a force sensor according to some embodiments of the instant disclosure.
Figure 12:
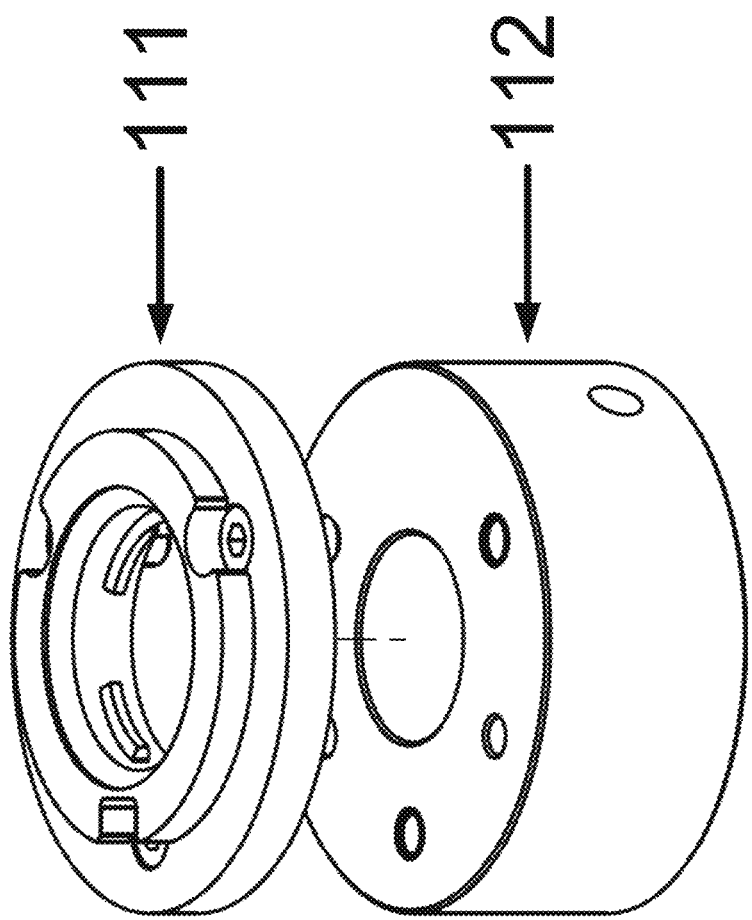
FIG. 12 illustrates an exploded view of a force sensor according to some embodiments of the instant disclosure.

During operation, the noise from the transmission shaft is minimized as much as possible so as not to cause problem when monitoring the motion of the surgical tool. In some embodiments, a sensor system can be used to monitor the surgical tool. FIG. 11 illustrates a cross-sectional view of a force sensor according to some embodiments of the instant disclosure. FIG. 12 illustrates an exploded view of a force sensor according to some embodiments of the instant disclosure. In some embodiments, the sensor system 110 is disposed between the end platform 130 and the adaptor 120. The sensor system 110 is configured to measure force of the adaptor 120. The sensor system 110 has a through hole where a receiving shaft 121 rotatably supported by a bearing 122 and a transmission shaft 140 rotatably supported by a bearing 131 meets.

In some embodiments, the sensor system 110 includes a force relay 111 and a force transducer 112 mechanically coupled to the force relay 111. The force relay 111 is detachably coupled to the adaptor 120. In some embodiments, the force relay 111 has grooves and protrusion that interlocks with grooves and protrusion of the adaptor 120.

In some embodiments, the force transducer 112 is mechanically attached to the force relay 111 and the end platform 130 and configured to convert an applied force to the adaptor 120 to an electrical signal. In some embodiments, the force transducer 112 is mechanically attached to the force relay 111 and the end platform 130 using fasteners 113 embedded around the periphery of the through hole of the force transducer 112. In some embodiments, a plurality of holes are formed on the front surface and back surface of the force transducer 112 to correspondingly accommodate fasteners 113 for the force relay 111 and the end platform 130. In some embodiments, the fasteners 113 for the force relay 111 interposes with the fasteners 113 for the end platform 130. In some embodiments, the fasteners 113 for the force relay 111 are not aligned and does not projectively overlap with the fasteners 113 for the end platform 130.

In some embodiments, the force transducer 112 is a donut load cell (also known as a load washer or thru-hole load cell). The force transducer 112 converts a force such as tension, compression, pressure, or torque into an electrical signal. In some embodiments, the force applied to the force transducer 112 is proportional to the change in the electrical signal.

In some embodiments, the applied force to the adaptor 120, aside from predetermined force and predetermined torque, further includes a force deviation and a torque deviation that is measured during operation. The force deviation indicates the influence in the direction of the receiving shaft when the surgical tool disposed on the receiving shaft 121 comes in contact with and exerts force on a target object, such as bone, during operation. The torque deviation indicates the influence in the motion of the receiving shaft when the surgical tool disposed on receiving shaft 121 comes in contact with and exerts force on target object, such as bone, during operation.

In some embodiments, the sensor system 110 is used in controlling the position and orientation of the surgical tool during operation. In some embodiment, the sensor system is signally connected to a controller. During operation, an operation plan with predetermined range, the predetermined path, or the combination thereof is received by the controller. The sensor system measures the force deviation, the torque deviation, or the combination thereof. The force deviation and the torque deviation are deviations from the predetermined range (i.e. predetermined force and predetermined torque) of the operation plan. The orientation and position of the surgical tool is adjusted based on the force deviation and the torque deviation. The orientation and position of the surgical tool is adjusted by controlling the actuators that moves the parallel manipulator. The movement of the surgical tool is adjusted by controlling the mechanical force from the shaft motor. In some embodiments, the transmission shaft may cause noise on the sensor system. Thus, in some embodiments, a low pass filter is further electrically coupled to the sensor system to remove noise.

Accordingly, one aspect of the instant disclosure provides a medical device that comprises a parallel manipulator having an end platform and a base platform mechanically coupled to the end platform; an adaptor having a body detachably coupled to the end platform and a receiving shaft rotatably supported by the body, the receiving shaft having a receiving yoke; a transmission shaft rotatably supported by the end platform, the transmission shaft having a transmission yoke configured to transfer mechanical force to the receiving yoke, a pliable rod coupled to the transmission yoke, and a runner coupled to the pliable rod; and a shaft motor configured to generate mechanical force to drive the transmission shaft, the shaft motor having a drive shaft slidably engaged to the runner.

In some embodiments, the medical device further comprises a sensor system disposed between the end platform and the adaptor, the sensor system is configured to measure force on the adaptor.

In some embodiments, the sensor system comprises a force relay detachably coupled to the adaptor; and a force transducer mechanically attached to the force relay and the end platform and configured to convert an applied force to the adaptor to an electrical signal.

In some embodiments, the transmission yoke has a protrusion and the receiving yoke has a groove structurally complementing the protrusion. In some embodiments, the transmission yoke is configured to transfer the mechanical force to the receiving yoke through a sidewall of the protrusion tangential to the groove when in motion.

In some embodiments, the runner has a socket. A sectional shape profile of the drive shaft is structurally complementary to a sectional shape profile of the socket. The socket is configured to slide along the drive shaft.

In some embodiments, the sectional shape profiles of the socket and the drive shaft are a polygonal shape profile.

In some embodiments, the drive shaft has a protrusion and the runner has a groove corresponding to the protrusion. In some embodiments, the protrusion is configured to slide along the groove.

In some embodiments, a minimum overlap between the drive shaft and the runner is no more than 5 mm.

In some embodiments, the pliable rod includes a spring tube having a plurality of layers.

In some embodiments, the medical device further comprises a barrel surrounding the runner. The barrel, the runner, and the drive shaft are successively fitted within one another.

In some embodiments, a young's modulus of the drive shaft is different from a young's modulus of the runner, and the young's modulus of the runner is different from a young's modulus of the barrel.

In some embodiments, the medical device further comprises lubricant applied to coat a surface of at least one of the barrel, the runner, and the drive shaft.

In some embodiments, at a minimum distance between the end platform and the base platform, the pliable rod is in normal state.

Accordingly, another aspect of the instant disclosure provides a medical device that comprises a parallel manipulator having an end platform and a base platform mechanically coupled to the end platform; a sensor system mechanically attached to the end platform; an adaptor detachably coupled to the sensor system, the adaptor having a body and a receiving shaft rotatably supported by the body; a transmission shaft rotatably supported by the end platform and configured to transfer mechanical force to the receiving shaft; and a shaft motor drivingly connected to the transmission shaft and configured to transfer mechanical force to the transmission shaft.

In some embodiments, the sensor system comprises a force relay detachably coupled to the adaptor; and a force transducer mechanically attached to the force relay and the end platform. The force transducer is configured to convert an applied force to the adaptor to an electrical signal.

In some embodiments, the force transducer is a donut load cell.

In some embodiments, the adaptor further has a bearing configured to rotatably attach the receiving shaft to the body. In some embodiments, the end platform further has a bearing configured to rotatably attach the transmission shaft to the end platform.

In some embodiments, the transmission shaft comprises a transmission yoke configured to transfer a mechanical force to the receiving shaft; a runner slidingly coupled to the shaft motor; and a pliable rod pinned to the transmission yoke and the runner.

In some embodiments, the medical device further comprises a barrel disposed on central area of the base platform. The barrel, the runner, and the drive shaft are successively fitted within one another.

In some embodiments, the medical device further comprises lubricant applied to coat a surface of at least one of the barrel, the runner, and the drive shaft.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A medical device, comprising:
   an adaptor configured to hold a surgical tool, wherein the adaptor includes:
      a body; and
      a receiving shaft rotatably supported by the body;
   a parallel manipulator, including:
      an end platform;
      a base platform; and
      a plurality of limbs operably coupled between the end platform and the base platform;
   a shaft motor attached to the base platform and configured to generate a mechanical force for manipulating movement of the surgical tool;
   a transmission shaft rotatably supported by the end platform, wherein the transmission shaft is configured to transfer the mechanical force to the receiving shaft; and
   a force transducer disposed between the adapter and the end platform and having a through hole, wherein the receiving shaft meets the transmission shaft in the through hole to receive the mechanical force from the transmission shaft to manipulate movement of the surgical tool.

2. The medical device according to claim 1, wherein the force transducer is a donut load cell and is configured to convert a force applied to the adaptor into an electrical signal.

3. The medical device according to claim 1, wherein the adaptor further has a first bearing configured to rotatably attach the receiving shaft to the body of the adaptor.

4. The medical device according to claim 1, wherein the adaptor further has a second bearing configured to rotatably attach the transmission shaft to the end platform.

5. The medical device according to claim 1, further comprising:
   a force relay disposed between the adaptor and the force transducer.

6. The medical device according to claim 5, wherein the force relay is detachably coupled to the adaptor, and the force transducer is mechanically attached to the force relay and the end platform.

7. The medical device according to claim 6, wherein the force transducer is mechanically attached to the force relay and the end platform using a plurality of fasteners embedded around a periphery of the through hole.

8. The medical device according to claim 7, wherein a plurality of holes are formed on a front surface and a back surface of the force transducer to correspondingly accommodate the plurality of fasteners for the force relay and the end platform.

9. The medical device according to claim 1, wherein the receiving shaft has a receiving yoke for receiving the mechanical force from the transmission shaft.

10. The medical device according claim 9, wherein the transmission shaft includes:
 a transmission yoke configured to transfer the mechanical force to the receiving yoke;
 a pliable rod connected to the transmission yoke; and
 a runner connected to the pliable rod.

11. The medical device according to claim 10, wherein the mechanical force generated by the shaft motor is transmitted to the runner through a drive shaft.

12. The medical device according to claim 10, wherein the pliable rod is a spring tube having a plurality of layers.

\* \* \* \* \*